United States Patent [19]

White et al.

[11] Patent Number: 5,045,775

[45] Date of Patent: Sep. 3, 1991

[54] ENVIRONMENTAL CORROSION MONITOR SYSTEM INCORPORATING DEPOSITED CONTAMINANTS AND CORROSION PRODUCTS

[75] Inventors: Malcolm L. White, Bethlehem, Pa.; Henry Leidheiser, Jr., Venice, Fla.

[73] Assignee: Lehigh University, Bethlehem, Pa.

[21] Appl. No.: 429,833

[22] Filed: Oct. 31, 1989

[51] Int. Cl.$^5$ ............................................. G01N 27/28
[52] U.S. Cl. .................................. 324/71.2; 324/700; 204/153.11; 204/404
[58] Field of Search ............................ 324/71.2, 700; 204/153.11, 404; 73/86

[56] References Cited

U.S. PATENT DOCUMENTS

| | | |
|---|---|---|
| 2,881,056 | 4/1959 | Joyner ........................................ 73/86 |
| 3,449,232 | 6/1969 | Bailey .......................... 204/153.11 X |
| 3,936,737 | 2/1976 | Jefferies, Sr. . |
| 4,065,373 | 12/1977 | Martin et al. . |
| 4,087,742 | 5/1978 | Khoo . |
| 4,181,882 | 1/1980 | Isaacs et al. . |
| 4,208,264 | 6/1980 | Polak et al. .......................... 204/404 |
| 4,380,763 | 4/1983 | Peart et al. . |
| 4,409,080 | 10/1983 | Slough . |
| 4,412,174 | 10/1983 | Conlon et al. . |
| 4,575,678 | 3/1986 | Hladky . |
| 4,611,175 | 9/1986 | Kumar et al. . |
| 4,652,823 | 3/1987 | Sutton . |
| 4,690,587 | 9/1987 | Petter et al. . |
| 4,800,165 | 1/1989 | Oka et al. . |
| 4,863,571 | 9/1989 | Chambaere .................... 204/153.11 |

OTHER PUBLICATIONS

The Corrosion Coulometer-A New Corrosion Monitor for Steel Structures; *ATLSS Report*, No. 88-07 (Oct. 1988).
Haruyama et al., A Corrosion Monitor Based on Impedance Method, 12-1981, pp. 167-186.
Gonzalez et al., Electrochemical Sensors for Atmospheric Corrosion Rates: A New Design, 5-1984, pp. 89-94.
Vassie, Corrosion of Structural Steelwork in Bridge Enclosures, Box Sections, and Anchorage Chambers, 11-1986, pp. 37-44.
Chandler, The Influence of Salts in Rusts on the Corrosion of the Underlying Steel, 7-1966, pp. 264-266.
Agarwala, A Probe For Monitoring Corrosion in Marine Environments, 12-1982, pp. 183-192.
Kucera et al., Practical Experience With an Electrochemical Technique For Atmospheric Corrosion Monitoring, 12-1981, pp. 238-255.
Ito et al., Diagnostic Analysis for Corrosion Deterioration of Steel Structures, 1-1987, pp. 64-70.
Mansfeld et al., Reproducibility of Electrochemical Measurements of Atmospheric Corrosion Phenomena, 12-1982, pp. 309-338.
Turcotte et al., Effects of Acid Deposition on Poultice-Induced Automotive Corrosion, 12-1986, pp. 200-212.
Raman, Atmospheric Corrosion Problems with Weathering Steels in Louisiana Bridges, 12-1988, pp. 16-29.

*Primary Examiner*—Kenneth Wieder
*Assistant Examiner*—Jack B. Harvey
*Attorney, Agent, or Firm*—Ratner & Prestia

[57] ABSTRACT

A system for monitoring and measuring the corrosion reaction of metals in an environment. The system includes a sample corrosion element of substantially the same material as the structure to be monitored, a galvanic cell for generating an electric signal indicative of the corrosion on the corrosion element, and a monitor for receiving and storing the generated signal. Moreover, the system is designed to incorporate corrosion products and environmental contaminants in order to simulate actual, localized conditions on a particular area of a structure.

10 Claims, 1 Drawing Sheet

ENVIRONMENTAL CORROSION MONITOR SYSTEM INCORPORATING DEPOSITED CONTAMINANTS AND CORROSION PRODUCTS

BACKGROUND OF THE INVENTION

The present invention relates to corrosion monitoring and measuring and, more particularly, to a compact system for detecting localized corrosion at various positions on civil engineering structural members, especially of steel material, in corresponding microenvironments.

The useful life of a structural member used in a corrosive microenvironment, which may differ from the environment extant only a short distance away, is necessarily limited by corrosion. It is economically desirable, however, that such a structural member be used as long as possible. Therefore, there is a demand for monitoring the status of corrosion of the structural member over long periods of time for the purpose of estimating the member's residual service life. To satisfy that demand, a corrosion monitor system should accurately measure the actual degree of corrosion at various positions on the structural member as it occurs in the microenvironments of use.

Unfortunately, one of the most difficult aspects of corrosion studies is the development of a system by which the resistance of different metals to certain corroding media and conditions can be evaluated. Because many variables are involved in the corrosion process, it is difficult to devise a system which will yield results commensurable with service conditions. Tests are often set up in the laboratory to show the effects of corrosion. When structures are placed in service under apparently identical conditions, however, the behavior may be quite different. In many instances, therefore, it is necessary to test structural materials in the service environment over extended time periods.

An observation frequently made concerning corrosion of structures, especially steel structures, is that the most serious attack on the structure occurs in areas where ionic contaminants (particularly chlorides), debris, and corrosion products have accumulated. In the case of weathering steels, severe localized corrosion may also occur. (A. Raman, *Degradation of Metals in the Atmosphere*, ASTM STP 965, S.W. Dean & T.S. Lee, Eds., 1988, pp. 16-29.) That problem has been studied in automobile bodies, where debris and road dirt can collect in crevices, wheel wells, and other entrapment areas. This accumulation is referred to as "poultice," and can cause severe corrosion of the automobile body, although the chemistry which occurs in the poultice is complex and varies with geographic location and whether the material is continually wet or has wet/dry cycles. (R.C. Turcotte, T.C. Comeau & R. Baboian, *Materials Degradation Caused by Acid Rain*, ACS Symposium Series 318, 1986, pp. 200-12.)

The same effects should occur for larger steel structures. The effects of ionic contaminants, particularly chlorides, on the "critical humidity" necessary for rusting of steels to occur have been well documented. (K.A. Chandler, Brit. Corros. J., 1, 264-66 (1966); P.R. Vassie, Brit. Corros. J., 22, 37-44 (1987).) In addition, chlorides accelerate corrosion. Any debris on the steel that holds moisture exacerbates the effect of ionic contaminants.

Despite the known influence of debris accumulation on corrosion, the corrosion monitors that are presently known do not include provisions for that effect. Devices exist that measure polarization curves (J.A. Gonzalez, E. Otereo, C. Cabans & J.M. Bastidas, Brit. Corros. J., 19, 89-94 (1984)), impedance (S. Haruyama & T. Tsuru, *Electrical Corrosion Testing*, ASTM STP 727, F. Mansfeld & U. Bertocci, Eds., 1981, pp. 167-86; S. Ito et al., Nippon Steel Technical Report No. 32, Jan. 1987), or time of wetness (F. Mansfeld et al., *Atmospheric Corrosion of Metals*, S.W. Dean & E.C. Rhea, Eds., ASTM STP 767, 1982, pp. 309-38; V. Kucera & J. Gullman, *Electrochemical Corrosion Testing*, F. Mansfeld & U. Bertocci, Eds., ASTM STP 727, 1981, pp. 238-55), but these devices do not include the effect of poultice on the output. A related investigation monitored marine corrosion by comparing the output of several galvanic cells in laboratory-simulated environments. (V.S. Agarwala, *Atmospheric Corrosion*, W.H. Ailor, Ed., 1982, pp. 183-92.) No attempt was made, however, to accumulate debris to simulate what might occur on a bridge structure.

The presently known corrosion monitors also include the use of galvanic cells to predict the rate at which corrosion will occur in a steel structure situated in a specific environment. Moreover, devices are capable of remote monitoring so that the progress of corrosion can more easily be followed over a long period of time. Some monitors operate in the same environment as the structures they intend to evaluate. None of the corrosion monitors collect corrosion products and environmental debris, however, even though the effects of those materials will influence the amount of corrosion which actually occurs.

SUMMARY OF THE INVENTION

The present invention comprises a compact corrosion monitor system which takes into account the effect of poultice (the accumulation of corrosion products, dirt, and miscellaneous environmental debris), geographic location, whether the structure monitored is continuously wet or experiences wet/dry cycles, and other localized environmental factors on the corrosion at particular positions on structural members. That object is accomplished by collecting the corrosion products and environmental contaminants within a cell containing a corrosion element of the same or similar, for evaluative purposes, material as the structure to be monitored. Accordingly, the environment of the corrosion element parallels the microenvironment of the structure.

Another object of the present invention is to record the amount of corrosion continuously over long periods of time so that the integrity of the structural member monitored may be followed. To accomplish that object, a galvanic cell is set up, with the corrosion element as one electrode, to generate an electric signal indicative of the corrosion occurring in the structure. The cell develops potential and current which arise when the cell is wet. The output signal generated by the galvanic cell is then monitored and recorded to determine the total amount of galvanic action which has occurred.

In order to allow transportation of the system easily and safely to the site where the structure is to be monitored, and use of the cell in any position, the components of the system are held together securely inside the cell and the cell has a compact construction.

Finally, by using standard materials, the system of the present invention may be constructed and used cheaply and easily.

These and other objects, features, and advantages of the present invention will become apparent in the following detailed description.

BRIEF DESCRIPTION OF THE FIGURE

A preferred embodiment of the present invention will be described, in detail, with reference to the drawing wherein.

DETAILED DESCRIPTION OF THE INVENTION

Figure 1:
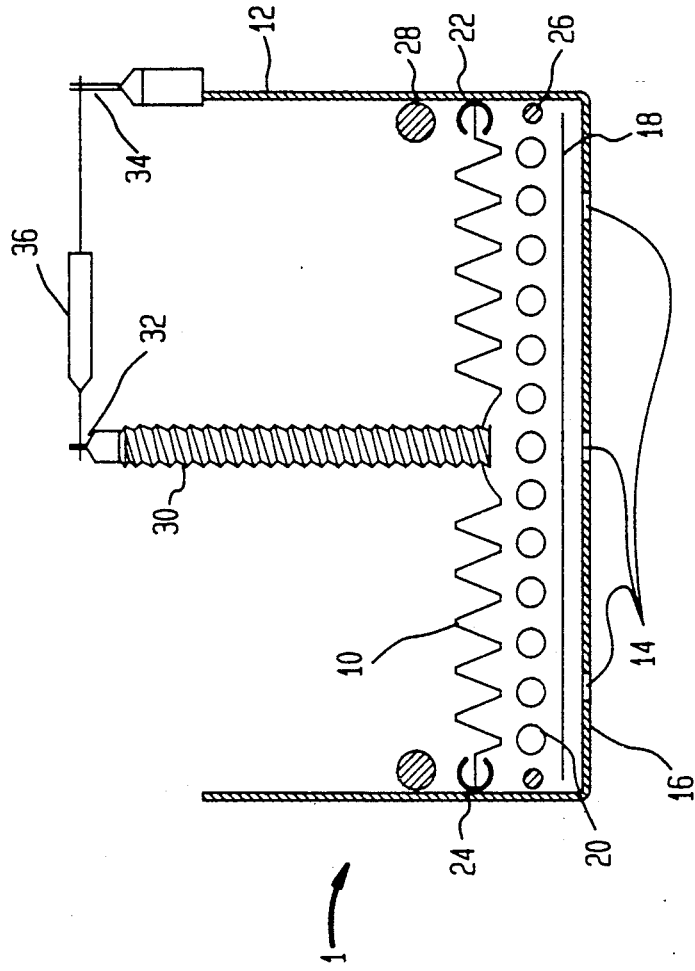
FIG. 1 is a schematic representation of the invention.

Referring to FIG. 1, a preferred embodiment of the present invention is shown as a corrosion monitor system 1. A corrosion element 10 is placed in the system and acts as one electrode of the galvanic cell. Corrosion element 10 is of the same or similar, for evaluative purposes, material as the structure to be monitored. If the structure to be tested is weathering or carbon steel, for example, then corrosion element 10 could be made of the corresponding material. Other materials, such as stainless steel or zinc, might also be used, however, as the corrosion element 10 even though the structure to be monitored is weathering or carbon steel. An advantage of using stainless steel or zinc as the corrosion element 10 is that such materials often last longer than other alternatives. Zinc would be especially useful to predict corrosion for galvanized steel structures.

It is preferred that corrosion element 10 have apertures so that corrosion products and environmental debris may collect underneath corrosion element 10 and water may drain. Accordingly, corrosion element 10 may be constructed, for example, of mesh screen. A piece of 14×14 mesh screen, cut into a 1½" diameter circle, is suitable. As would be known, however, it is also possible to allow the corrosion products and environmental debris to collect underneath corrosion element 10 and water to drain by, for example, beveling or sloping corrosion element 10.

Corrosion element 10 is placed inside a cup 12. Cup 12 forms the basic container for the corrosion system 1 components and the second electrode for the galvanic cell. A standard 1¾" diameter cup (obtained from a plumbing supply house) is suitable. The inside of cup 12 should be cleaned by abrading with steel wool or fine SiC paper. Several holes 14 (3/16" diameter suffices) are drilled in the bottom 16 of cup 12 to allow drainage.

A piece of porous, non-reactive, long-lived cloth or filter paper 18 is cut to fit inside the bottom 16 of cup 12 under corrosion element 10. Whatman #4 filter paper is suitable. Filter 18 will allow water to drain while retaining corrosion products and debris. On top of filter 18 and under corrosion element 10 is placed at least one layer of beads 20. Beads 20 may be made of solid glass, 3 mm in diameter. Beads 20, like filter 18, serve to collect corrosion products and debris.

An insulator 22 is mounted on the side edges 24 of corrosion element 10 along its perimeter to prevent corrosion element 10 from contacting cup 12. Insulator 22 may be constructed of ⅛" outside diameter and 1/32" wall thickness non-reactive, long-lived tubing, such as tygon tubing, slit open to surround corrosion element 10. At least one spacer 26 is placed around the perimeter of beads 20 to keep beads 20 away from the inner perimeter of cup 12 so that better contact is made between beads 20 and corrosion element 10. Otherwise, insulator 22 might rest on beads 20 and hold corrosion element 10 away from beads 20. An "O" ring, 3/32" thick and 1⅜" outside diameter, is suitable to form insulator 22.

A retainer 28 is forced into cup 12 over corrosion element 10 to hold all the components of system 1 together in the galvanic cell. Thus, system 1 may be used in any position and can be transported without damage to the components. Retainer 28 may be formed from a second "O" ring, ⅛" thick and 1 11/16" outside diameter.

To make electrical connection to corrosion element 10, a connecting element 30 is placed in contact with corrosion element 10. Connecting element 30 may be a machine screw constructed of cold rolled or stainless steel. To assure electric contact, one end of connecting element 30 may be placed through the mesh of corrosion element 10. At its opposite end, connecting element 30 engages a first connector 32. First connector 32 may be, for example, a Mueller alligator clip. When a second connector 34 (preferably a copper Mueller clip) is fastened to the edge of cup 12 (preferably with a copper screw, not shown), two connections of a galvanic cell are formed with corrosion element 10 acting as one electrode and cup 12 acting as the other electrode. Thus, it is possible not only to measure the potential and current developed when the galvanic cell is wet and galvanic corrosion is occurring, but to determine the total amount of galvanic action occurring, as described in the following paragraph.

In order to make informative use of the electrical output of the galvanic cell, a monitor 36 is provided. One end of monitor 36 is attached to first connector 32, while the opposite end of monitor 36 is fixed to second connector 34. In order to monitor the electrical output of the galvanic cell continuously, monitor 36 may be a microcoulometer. An E-cell (Series 560, Pacific Electron Corporation, Sterling Heights, MI 48077), which operates on the principle of plating silver on a gold electrode to accumulate quantitatively the number of coulombs (current×time) generated by the galvanic cell, may be chosen. The galvanic cell may then be "read" and "cleared" for the next cycle by a controlled deplating to measure the amount of accumulated charge in microcoulombs. The coulometric data are a convenient way to measure the total output of the galvanic cell. When used in such a way, the system 1 may be called a "corrosion coulometer".

In operation, when saturated with water, the galvanic action between cup 12 and corrosion element 10 creates a current. That current output may be monitored. As the galvanic cell dries out, the current output decreases until it stops when the galvanic cell is completely dry. The total output of the galvanic cell can be stored in a microcoulometer, which can then be read at any time. As corrosion element 10 corrodes, corrosion products and environmental contaminants collect on the corrosion element 10, on beads 20, and on underlying filter 18, to simulate environmental conditions of accumulation.

Analyses conducted by the present inventor on steel structures indicate good correlation between the output signal of the present invention and actual corrosion. (M.L. White & H. Leidheiser, Jr., *The Corrosion Coulometer—A New Corrosion Monitor for Steel Structures*, ATLSS Rep. No. 88-07 (Oct. 1988).) The correlation was better than that achieved by prior art devices which failed to accumulate corrosion products and environmental contaminants.

A single preferred embodiment of the present invention has been disclosed herein. It is to be understood, however, that various changes and modifications may be made without departing from the true scope and spirit of the present invention as set forth and defined in the following claims:

What is claimed is:

1. A corrosion monitor system for measuring the effect of corrosion in a structure, which comprises:
    a corrosion element of substantially the same material as the structure to be monitored and having means for allowing corrosion products and environmental contaminants and debris to collect underneath said corrosion element;
    a galvanic cell, for generating an electric signal indicative of the corrosion on said corrosion element, having as a first electrode said corrosion element;
    means for collecting corrosion products and environmental contaminants and debris within said galvanic cell underneath said corrosion element while allowing water to drain away from said corrosion element whereby the environment of said corrosion element parallels the environment of said structure; and
    means for receiving and storing said electric signal generated.

2. A corrosion monitor system according to claim 1, wherein said galvanic cell further comprises:
    a second electrode substantially surrounding said corrosion element;
    an electrical connector in electric contact with said corrosion element at its lower end and extending above said corrosion element at its upper end;
    a first connector mounted on said upper end of said electrical connector;
    a second connector mounted on said second electrode;
    whereby said first and said second connectors form connections by which the electrical output of the cell may be received and stored.

3. A corrosion monitor system as claimed in claim 2, wherein said corrosion element is steel and said second electrode is copper.

4. A corrosion monitor system as claimed in claim 1, wherein said receiving and storing means comprises a microcoulometer placed in electrical connection with said galvanic cell for continuously monitoring the electrical output of said galvanic cell.

5. A corrosion monitor system for measuring the effect of corrosion in a structure, which comprises:
    a corrosion element of substantially the same material as the structure to be monitored and having means for allowing corrosion products and environmental contaminants and debris to collect underneath said corrosion element;
    a galvanic cell, for generating en electric signal indicative of the corrosion on said corrosion element, having as a first electrode said corrosion element;
    means for collecting corrosion products and environmental contaminants and debris within said galvanic cell, said collecting means including:
    (a) a cup surrounding said corrosion element,
    (b) a filter placed inside said cup under said corrosion element,
    (c) a plurality of beads forming at least one layer located inside said cup, over said filter, and contacting the underside of said corrosion element,
    (d) at least one spacer positioned inside said cup to force said beads away from the periphery of said cup and to assure contact between said beads and said corrosion element,
    (e) an insulator mounted between the side edges of said corrosion element and the inner surface of said cup to prevent contact between said corrosion element and said inner surface of said cup, and
    (f) a retainer inserted inside said cup over said corrosion element to force said corrosion element, said beads, said filter, said spacers, and said insulator in fixed position inside said cup despite movement of said cup, whereby the environment of said corrosion element parallels the environment of said structure; and
    means for receiving and storing said electric signal generated.

6. A corrosion monitor system as claimed in claim 5, wherein said cup has holes suitable for draining.

7. A corrosion monitor system as claimed in claim 5, wherein said cup is copper and said corrosion element is steel.

8. A corrosion monitor system for measuring the effect of corrosion in a structure, which comprises:
    a corrosion element of substantially the same material as the structure to be monitored, said corrosion element forming a first electrode of a galvanic cell and having means for allowing corrosion products and environmental contaminants and debris to collect underneath said corrosion element;
    a cup of a preselected material forming a second electrode of said galvanic cell and surrounding said corrosion element;
    a microcoulometer connected at a first end to said corrosion element and connected at its opposite end to said cup for continuously measuring the electric output between said cup and said corrosion element;
    a filter placed inside said cup under said corrosion element;
    a plurality of beads forming at least one layer located inside said cup, over said filter, and contacting the underside of said corrosion element;
    at least one spacer positioned inside said cup to force said beads away from the periphery of said cup and to assure contact between said beads and said corrosion element;
    an insulator mounted between the side edges of said corrosion element and the inner surface of said cup to prevent contact between said corrosion element and said inner surface of said cup; and
    a retainer inserted inside said cup over said corrosion element to force said corrosion element, said beads, said filter, said spacers, and said insulator in fixed position inside said cup despite movement of said cup.

9. A corrosion monitor system as claimed in claim 8, wherein said corrosion element is steel and said cup is copper.

10. A corrosion monitor system as claimed in claim 8, wherein said cup has holes suitable for draining.

* * * * *

UNITED STATES PATENT AND TRADEMARK OFFICE
CERTIFICATE OF CORRECTION

PATENT NO. : 5,045,775
DATED : September 3, 1991
INVENTOR(S) : Malcolm L. White and Henry Leidheiser, Jr.

It is certified that error appears in the above—identified patent and that said Letters Patent is hereby corrected as shown below:

Column 4, line 2: delete "insulator 22: and insert --spacer 26--; and

Column 4, line 60: delete "inventor" and insert --inventors--,

Signed and Sealed this

Second Day of March, 1993

*Attest:*

STEPHEN G. KUNIN

*Attesting Officer*    Acting Commissioner of Patents and Trademarks